(12) United States Patent
Bercovy et al.

(10) Patent No.: US 8,540,776 B2
(45) Date of Patent: Sep. 24, 2013

(54) TOTAL KNEE PROSTHESIS

(76) Inventors: Michel Bercovy, Paris (FR); Luc Kerboull, Paris (FR); David Bracy, Victoria (AU)

( * ) Notice: Subject to any disclaimer, the term of this patent is extended or adjusted under 35 U.S.C. 154(b) by 143 days.

(21) Appl. No.: 12/996,161

(22) PCT Filed: Jun. 3, 2009

(86) PCT No.: PCT/FR2009/951052
§ 371 (c)(1),
(2), (4) Date: Feb. 11, 2011

(87) PCT Pub. No.: WO2010/001010
PCT Pub. Date: Jan. 7, 2010

(65) Prior Publication Data
US 2011/0125278 A1 May 26, 2011

(30) Foreign Application Priority Data
Jun. 6, 2008 (FR) ...................... 08 53766

(51) Int. Cl.
*A61F 2/38* (2006.01)
(52) U.S. Cl.
USPC ...................................... 623/20.21
(58) Field of Classification Search
USPC ................. 623/20.11–20.31, 20.21
See application file for complete search history.

(56) References Cited

U.S. PATENT DOCUMENTS

| 5,203,807 A | 4/1993 | Evans et al. |
| 6,152,960 A | 11/2000 | Pappas et al. |
| 6,616,696 B1 | 9/2003 | Merchant et al. |
| 6,893,467 B1 * | 5/2005 | Bercovy ...................... 623/20.14 |
| 2007/0135926 A1 * | 6/2007 | Walker ........................ 623/20.31 |
| 2008/0243259 A1 * | 10/2008 | Lee et al. .................... 623/20.32 |

FOREIGN PATENT DOCUMENTS

| EP | 0 522 822 | 1/1993 |
| EP | 1 354 371 | 10/2003 |
| EP | 1 611 871 | 1/2006 |
| FR | 2 852 819 | 10/2004 |
| WO | 00/13616 | 3/2000 |
| WO | 00/23011 | 4/2000 |
| WO | 02/060002 | 8/2002 |
| WO | 2005/122967 | 12/2005 |

\* cited by examiner

*Primary Examiner* — Bruce E Snow
*Assistant Examiner* — Brian Dukert
(74) *Attorney, Agent, or Firm* — Clark & Brody

(57) ABSTRACT

The present invention relates to a total knee prosthesis. This prosthesis includes a femoral implant (2) including two condyles (8, 9) delimiting between them an intercondylar notch (10), a tibial implant (3) intended to rest on the end of the tibia, and an articular insert (4) interposed between the tibial implant and the femoral implant and the upper surface of which (41) includes two glenoid cavities (18, 19) with an external profile (181, 191) congruent with the external profile (81, 91) of the condyles (7, 8) of the femoral implant and connected together through an interglenoidal connecting surface (20). According to the invention, the intercondylar notch (10) and the interglenoidal connecting surface (20) have congruent contact surfaces (101, 201) which are inscribed in two mating hyperbolic paraboloids and the contact surface (181, 191) of the glenoid cavities (18, 19) have in a horizontal section an ovoid shape and its inclined point (P) is located posteriorly to the line of larger width (L) of the insert.

9 Claims, 3 Drawing Sheets

TOTAL KNEE PROSTHESIS

FIELD OF THE INVENTION

The present invention relates to the field of joint prostheses, and more particularly in this particular field, to a novel total knee prosthesis.

BACKGROUND ART

Prostheses for the joint of the knee have to be designed in order to observe two main rules:
- a tribological rule: they have to undergo minimum wear during use;
- a kinematic rule: the operation of the prosthesis should be as comfortable as possible for the patient in all daily activities.

And above all, tribology should meet kinematics and conversely kinematics should be compliant with tribology. It is within the scope of this dual converse obligation that the present invention is located.

In this field of knee prostheses, many prior proposals of total knee prosthesis have already been made. These total prostheses traditionally include three functional elements: a femoral element intended to be implanted on the lower end of the femur, a tibial element adapted so as to be implanted on the upper end of the tibia, and finally an articular insert, generally in polyethylene intended to be inserted between the femoral element and the tibial element. The articular insert is conformed in order to allow and guide movements of the femoral element with respect to the tibial element in all the movements of the prosthetic joint in flexure and/or rotation according to kinematics as close as possible to those of the anatomical knee.

For this purpose, the femoral element includes two condyles, medial and lateral condyles respectively, delimiting between them a so-called intercondylar notch and the articular insert itself has an upper surface including two glenoid cavities, the surfaces of which are of a shape substantially mating the external surfaces of the condyles of the femoral implant and connected together through a protruding interglenoidal connecting surface intended to be housed in the intercondylar notch.

Moreover, the articular insert also has a lower surface configured in order to co-operate with the tibial element. The latter has a planar supporting plate of the insert in which a substantially cylindrical orifice is formed and the lower surface of the insert, as for it, is planar and includes a pin for blocking and pivoting the insert on the tibial element intended to be inserted into the orifice of the tibial element.

In a way known per se, the compliance or congruence between the contact surfaces of the femoral component and the insert is a determining element allowing reduction of wear of the articular surfaces, notably of the insert. Consequently, as the surfaces are more or less fitted into each other, releasing the movement is accomplished by pivoting the insert on the tibial component around a vertical axis, whether it is central or shifted sideways.

Such knee prostheses are traditionally said to be with a "mobile plate" and the prosthesis of the present invention is preferentially of this type.

Depending on the patients to be implanted, the prosthesis may finally include a patellar component covering the posterior portion of the patella and intended to be jointed with the femoral element in its trochlear portion up to a flexural angle of about 60°, and then partly with the condylar portion beyond this flexural angle.

With the purpose of allowing a more or less physiological movement of the joint, several solutions have been proposed in the state of the art.

A first of these configurations consists of forcing the displacement of the femoral element of the prosthesis on the upper surface of the articular insert via a cam formed by a pin or ramp located between the glenoid cavities of the insert, this cam co-operating with a transverse abutment formed in the intercondylar notch of the femoral element. This type of prostheses is said to be "postero-stabilized".

This prosthesis configuration does not allow the prosthetic knee to adapt to all the movements since it imposes a constant posterior displacement; further the flexion-extension movements of the joint are movements constrained by the co-operation of the cam and of the abutment, therefore unidirectional and identical movements under all circumstances and which may therefore provide bothersome abutment and repulsion sensations, notably at the patella.

Another configuration consists of producing a knee prosthesis said to be with "guiding surfaces", i.e. for which only the topography of the contact surfaces of the femoral and tibial elements and of the insert of the prosthesis are involved in solving physiological, tribological and stability requirements of the prosthetic joint.

Such prostheses with guiding surfaces are generally without any planar contact surface, any protruding edges and/or abutment element on the articular surfaces of the femoral element (condyles, intercondylar notch, and femoral trochlea) as well as on the upper surface of the articular insert (glenoid cavities and interglenoidal connecting surface).

Among the latter, document WO 00/23 011 describes a prosthesis including a contact surface between insert and femoral component such that the contact point between femoral component and insert is shifted forwards or backwards in each adjacent sagittal plane. This configuration provides point-like or linear and non-surface contacts between femoral element and insert of the prosthesis, responsible for high pressure points, therefore strong point-like or cutting mechanical stresses on the articular insert of the prosthesis, accelerating wear of the latter.

In other proposals such as patent applications FR 2 852 819, and WO 2005/122 967 the femoral component is laid in a cup at the upper face of the insert, in which it is maintained by a wall formed with the whole of the anterior portion of the insert which prevents any rotary movement between both of these portions, without generating a specific movement.

Finally, other proposals such as the one described in document EP 1 354 371 A1, have avoided any central contact between the dome of the insert and the intercondylar notch of the component which suppresses the central guiding effect of the dome of the insert and amounts to having a bicondylar prosthesis bearing upon both glenoids. Moreover, in this type of prosthetic joint of the knee, the medial and lateral condylar supports in the glenoid cavities of the insert are asymmetrical, creating several sources of problems. One of them lies in the fact that a loosening torque is created by compression in the medial cavity, clearly greater than the compression in the lateral cavity. Consequently, the tibial element tends to loosen on the (external) lateral edge of the knee.

Moreover, most of these prostheses have satisfactory congruence in the areas close to the extension, but this congruence substantially decreases upon flexure because of the gradual reduction of the condylar radii of curvature, in the posterior portion of the joint, while the radius of curvature of the tibial plate remains constant.

SUMMARY OF THE INVENTION

The object of the present invention is to propose a novel total knee prosthesis of the type with a mobile plate and guiding surfaces, which does not have the aforementioned drawbacks of the known total prostheses from the prior art.

Most particularly the goal of the invention is to improve the comfort for the person wearing the prosthesis, by promoting unconstrained operating kinematics of the prosthesis, which at best meets all the physiological, tribological and stability requirements of the prosthetic joint.

Another goal of the present invention is also to provide a novel total knee prosthesis which prevents so-called "roll-forward" phenomena i.e. anterior sliding of the femoral element of the prosthesis upon flexural movements, without using any abutment or cam surface at the joint surfaces of the femoral element and of the insert of the prosthesis.

In order to meet these goals, the present invention proposes a novel total knee prosthesis of the type including:

- a femoral implant including two condyles delimiting between them an intercondylar notch, the external profile of which is convex in a sagittal plane and concave in a frontal plane and connects in all the planes without any discontinuity with the external profile of the condyles,
- a tibial implant including at least one supporting plate intended to rest with its lower surface on the end of the tibia, if necessary after resection, and
- an articular insert interposed between the tibial implant and the femoral implant and capable of co-operating with them through lower and upper contact surfaces of mating shapes respectively of the upper surface of the supporting plate of the tibial implant and external profiles of the condyles and of the intercondylar notch of the femoral implant,
- the upper surface of the joint insert including two glenoid cavities with an external profile congruent with the external profile of the condyles of the femoral implant and connected together through a protruding interglenoidal connecting surface, with a shape congruent with that of the intercondylar notch, and with an external profile convex in a frontal plane and concave in a sagittal plane and connecting in all the planes without any discontinuity with the external profile of the glenoid cavities.

According to the prosthesis of the invention and in a characteristic way thereof, the intercondylar notch and the interglenoidal connecting surface have congruent contact surfaces which define two complementary hyperbolic paraboloids and in that the contact surface of the glenoid cavities of the insert with the condyles have in a horizontal cross-section an ovoid shape, the major axis of which is oblique towards the top and front of the insert and its inclined point is located posteriorly to the line of larger width of the insert regardless of the flexural angle of the femoral implant with respect to the tibial implant and the insert.

Thus, three distinct mechanical situations are obtained during the movements of the joint of the knee:

1/ in an extension position, a stable mechanical balance is obtained by the joint surfaces of the femoral component completely fitting into the insert, over the whole width of the glenoid cavities, and of the central interglenoidal surface of the insert, between these cavities;

2/ from the moment when, under the action of muscles, the knee is no longer in this extension position, it is in an unstable mechanical situation and is guided by the effect of gravity towards a mechanical balance position.

3/ at the end of flexure, the knee is in a balanced position by stabilization of the femoral condyles at gravitational wells provided in each of the glenoid cavities of the insert and as defined hereafter.

According to a first preferred feature of the prosthesis of the invention, the lowest points, in two adjacent sagittal planes, of the contact surface of the glenoid cavities of the insert are all located on a same straight line in a same transverse plane of the insert.

According to another advantageous feature, the ovoid contact surfaces of the glenoid cavities of the insert are connected, at each flexure level, through a concave isthmian surface both forwards and backwards and inscribed in the hyperbolic paraboloid defined by the interglenoidal connecting surface. This allows transmission of the stresses into the central portion of the prosthesis, but also axial rotation about a vertical axis which may be central or shifted towards one of the glenoids.

Still according to the invention and to a preferred embodiment thereof, the width of the interglenoidal connecting surface, taken in a horizontal plane, is decreasing from the anterior portion to the posterior portion of the insert. With this feature, it is notably possible to efficiently combat roll-forward phenomena of the femoral element during flexural movements.

With the same goal, another advantageous feature of the invention consists in that the straight line ($\Delta$) passing through the highest points of the interglenoidal connecting surface has a slope which decreases from the anterior portion toward the posterior portion of the insert.

Preferably, this straight line ($\Delta$) in a preferred embodiment forms an angle comprised between 1° and 15°, and preferably further comprised between 4° and 10°.

Still according to the invention, the total knee prosthesis also includes a patellar implant adapted for co-operating through an articular surface with the femoral implant, the articular surface of said patellar implant being a hyperboloic paraboloid mating the one defined by the intercondylar notch in order to allow continuous contact in the sagittal and horizontal planes of the patellar implant and of the femoral implant from the highest portion of the trochlea up to the posterior portion of the condyles in all the flexural positions, the contact being made over the whole of the height and the whole of the width of the articular face of the patella.

Finally, still according to the invention, the tibial implant of the prosthesis of the invention includes on a lower face side, stabilization reinforcements. Advantageously, these reinforcements are oriented towards the base of the gravitational well of the insert, i.e. inclined points of each of the glenoid cavities of the insert. Such side reinforcements notably give the possibility of relieving the increases in stresses which tend to generate a torque for loosening the tibial implant upon flexural movements of the prosthetic joint.

BRIEF DESCRIPTION OF THE DRAWINGS

Various other features of the prosthesis of the present invention will become apparent upon reading the detailed description which follows, made with reference to the appended figures, which show, as non-limiting examples, embodiments of the prosthesis of the invention. Among the appended drawings.

DETAILED DESCRIPTION OF THE INVENTION

As this is apparent from the figures, the object of the invention relates to a total prosthesis 1 of the knee conventionally comprising a femoral implant 2 and a tibial implant 3, both preferably consisting of a biocompatible stainless metal alloy, and an articular insert 4, generally in a plastic material such as polyethylene. However, one or more elements of this prosthesis may also consist of alumina ceramic or of alumina and zirconia ceramic or biocompatible resins for example.

The femoral implant 2 and the tibial implant 3 are both intended to be adapted after resection, onto the femoral low epiphysis and the tibial upper epiphysis, respectively.

Figure 2:
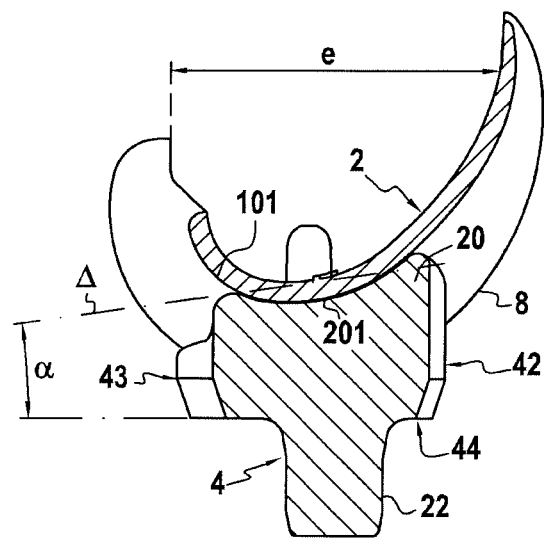
FIG. 2 illustrates a median longitudinal sectional view along the plane II of FIG. 1.

The femoral implant 2 seen from the side as partly illustrated in FIG. 2 has a substantially non-symmetrical U-shape between the branches of which a housing 5 is delimited for attachment onto the lower epiphysis of the femur, in particular by fitting two protruding lugs 6 into each other.

The femoral implant 2 also includes an articular lower face 7 producing two condyles, respectively a medial condyle 8 and a lateral condyle 9, separated and attached to each other through an intercondylar notch 10. Both medial and lateral condyles 8, 9 of the femoral implant are conformed so that their section along a sagittal plane, has the shape of a single turn, the radius of curvature of which decreases from the anterior extreme portion of the implant forming the femoral trochlea 11 towards the posterior portion of the implant.

At the anterior portion of the femoral implant 2, the femoral trochlea 11 thus extends in the anterior extension of both condyles 8, 9 and includes two medial 12 and lateral 13 trochlear cheeks extending without any discontinuities the external profile of the medial and lateral condyles 8, 9 respectively. Both trochlear cheeks 12, 13 are brought together by a trochlear throat 14 itself extending without any discontinuities in the anterior extension of the intercondylar notch 10. Thus, the femoral trochlear throat extends the hyperbolic paraboloid shape of the intercondylar notch forwards without any breaks in shape, continuity or angulation, from the highest portion of the trochlea right up to the most posterior portion of the condyles.

Figure 6:
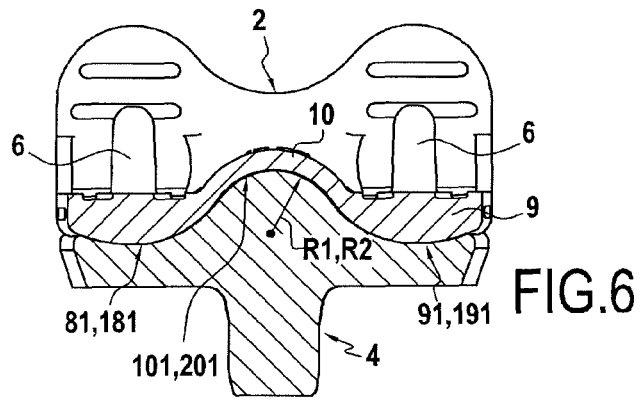
FIG. 6 illustrates a sectional view of the femoral implant and of the insert of the prosthesis of the invention along a frontal plane VI-VI in FIG. 4 comprising the axis of rotation of the pin of the insert.

As this is illustrated in FIG. 6, each condyle 8, 9 has in a frontal plane, i.e. transversely to the sagittal plane, a convex and rounded profile 81, 91. Between the condyles, the intercondylar notch 10, as for it, has in a frontal plane, a concave and rounded profile 101, which is connected without any discontinuities or any edges with that of both medial and lateral condyles 8, 9.

Thus, the femoral element 2 is such that in a frontal plane, the external plane 101 for connecting the intercondylar notch 10 with the external profile 81, 91 of the condyles 8, 9 has a constant radius of curvature R1 from the anterior portion to the posterior portion of the femoral implant 2.

Figure 7:
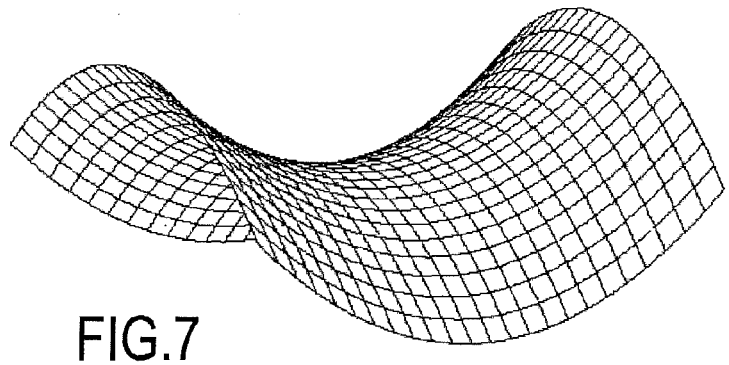
FIG. 7 illustrates a hyperbolic paraboloid surface compliant with the surfaces of mutual contact of the intercondylar notch and of the central interglenoidal connecting dome of the insert of the prosthesis of the invention.

According to the present invention, the external profile 101 of the intercondylar notch 10 is such that the latter defines a median contact surface of the femoral implant 2 with the shape of a hyperbolic paraboloid, as illustrated in FIG. 7, to which the convex external profiles 81, 91 (in a frontal plane) of the condyles 8, 9 are laterally connected without any discontinuities or edges.

Also, the surface profile 15 of the trochlear throat 14 also has, on the anterior portion of the femoral implant, a hyperbolic paraboloid shape to which the convex profiles of the medial and lateral trochlear cheeks 12, 13 are laterally connected in the anterior extension of the condyles 8, 9.

In a conventional way, known per se, the femoral implant 2 is intended to co-operate with the articular insert 4 and more particularly to move on the upper surface 41 of the latter according to a rolling-sliding movement of the condyles 8, 9 and of the intercondylar notch 10 on portions 18, 19, 20 of complementary shape formed on the upper surface 41 of the articular insert.

For this purpose, the insert 4 of the prosthesis according to the invention includes on its upper surface two glenoid cavities 18, 19, respectively a medial cavity 18 and a lateral cavity 19, separated from each other along the median axis of the insert by an interglenoidal connecting surface 20 formed by a protruding dome inserted inbetween both glenoid cavities 18, 19.

In a frontal plane, the external profile 201 for connecting the interglenoidal surface 20 with the external profile 181, 191 of the glenoid cavities 18, 19 of the articular insert has a radius of curvature R2 which is constant from the anterior portion 42 to the posterior portion 43 of the insert.

Preferably, the radius of curvature R2 of the external profile 201 for connecting the interglenoidal surface 20 with the external profile 181, 191 of the glenoid cavities 18, 19 of the articular insert 4 and the radius of curvature R1 of the external profile 101 for connecting the intercondylar notch 10 are substantially equal in common frontal planes so that the intercondylar notch 10 forms an imprint of the interglenoidal surface 20 between both condyles 8, 9 of the femoral implant. However, it is also possible to provide a radius of curvature R1 which is variable, preferably in a decreasing way, from the anterior portion towards the posterior portion of the femoral implant, just like moreover the radius R2 of the interglenoidal connecting surface of the insert.

According to the present invention, the interglenoidal surface 20 has a congruent contact surface 201 of the contact surface 101 of the intercondylar notch 10 of the femoral implant 2 and which more particularly defines a second hyperbolic paraboloid, mating the one defined by said notch 10. This surface 201 like the surface 101 of the intercondylar notch is inscribed in a hyperbolic paraboloid surface as illustrated in FIG. 7.

Further still according to the invention, the contact surface 181, 191 of each of the glenoid cavities 18, 19 of the insert 4 is conformed so that in a horizontal section, this surface has an ovoid shape and that the inclined point, i.e. its lowest point of this surface forms a gravitational well P located in the posterior third of the insert, in practice set back from the line L of largest width of the insert.

The configuration of the articular surfaces of the femoral implant 2 and of the articular insert 4 of the prosthesis 1 of the present invention thereby gives the possibility of providing to the operating prosthetic joint, kinematics and stability particularly close to those of the anatomical joint.

More specifically, these articular surfaces 81, 91, 101 and 181, 191, 201 provide an unstable balance between the femoral implant 2 and the articular insert 4 from the moment that the knee is no longer in complete extension so that the oscillation of the femoral component 2 only occurs by rolling in the antero-posterior direction of the femoral condyles 8, 9 in the glenoid cavities 18, 19 by guiding the condyles over the ovoid contact surfaces 181, 191 towards the gravitational well P made in the posterior third of said cavities rearwards from the widest portion of the insert. This action is only produced by the action of gravity on the femoral element in an unstable balance and does not include any cam effect.

Thus, during the flexural movements of the prosthetic joint of the knee according to the present invention, the rolling movement of the femoral condyles 8, 9 in the glenoid cavities 18, 19 of the insert is perfectly stabilized by the complete congruence of the contact surfaces 81, 91, 101 and 181, 191, 201 of the femoral implant 2 and of the insert 4 in all the flexure/extension positions.

The glenoid cavities of the insert of the prosthesis 1 of the invention are also formed so that the lowest points in two adjacent sagittal planes, of their contact surface 181, 191 are located on a same straight line in a same median plane of the insert. Further, these ovoid contact surfaces of the glenoid cavities of the insert are connected to the surface 201 of the surface 20, at each flexural level through an isthmian surface concave towards the front and rear and inscribed in the hyperbolic paraboloid defined by the interglenoidal surface.

Both medial and lateral cavities 18, 19 thereby form for the femoral condyles 8, 9 two ovoid guide ramps each oriented along two major axes D1, D2 which diverge relatively to each other with respect to the median sagittal plane of the insert 4 from the anterior face 42 to the posterior face 43 of the latter and inclined from top to bottom towards the gravitational well P of each of them.

Perfect congruence of the articular surfaces of the femoral implant 2 and of the articular insert 4 and guiding conformation of the ovoid contact surfaces 181, 191 of the glenoid cavities 18, 19 of said insert toward natural balance points such as the gravitational wells P in the posterior third of said cavities thereby provide to the prosthesis 1 of the invention unconstrained kinematics and adequate stability very close to those of the anatomical joint.

Moreover, the perfect congruence of the intercondylar notch 10 and of the interglenoidal surface 20, for which the surface profiles defined two mating hyperbolic paraboloids, are also involved in the stabilization of the antero-posterior rolling movements of the femoral implant 2 on the insert 4 but also allow a medio-lateral lift-off allowing observance of natural lift-off of the joint of the knee during which the support of the condyle is not only glenoidal but also central, promoting central transmission of the stresses and thereby avoiding generation of a torque loosening the tibial implant from the bone surface of the tibia.

Furthermore, the width Is of the interglenoidal surface 20, taken in a horizontal plane, is advantageously decreasing from the anterior face 42 to the posterior face 43 of the insert 4, and further the interglenoidal surface 20 is such that the straight line Δ passing through the highest points of the interglenoidal dome has a decreasing slope from the anterior face to the posterior face of the insert and preferably by forming an angle α with the lower surface 44 of the insert comprised between 4° and 10°.

Both of these features of the interglenoidal surface 20 notably allow efficient combat of roll-forward phenomena of the femoral element 2 during flexural movements of the knee.

Indeed, the slightly raised but especially wider configuration of the interglenoidal surface 20 of the anterior face 42 of the insert towards the posterior face 43 is also involved in guiding the condyles 8, 9 towards the gravitational well P of the glenoid cavities 18, 19 while opposing forward sliding (roll-forward) of the femoral implant 2 on the insert 4 during flexure, which further increases the stability of the prosthetic joint formed by the prosthesis 1 of the invention.

Figure 1:
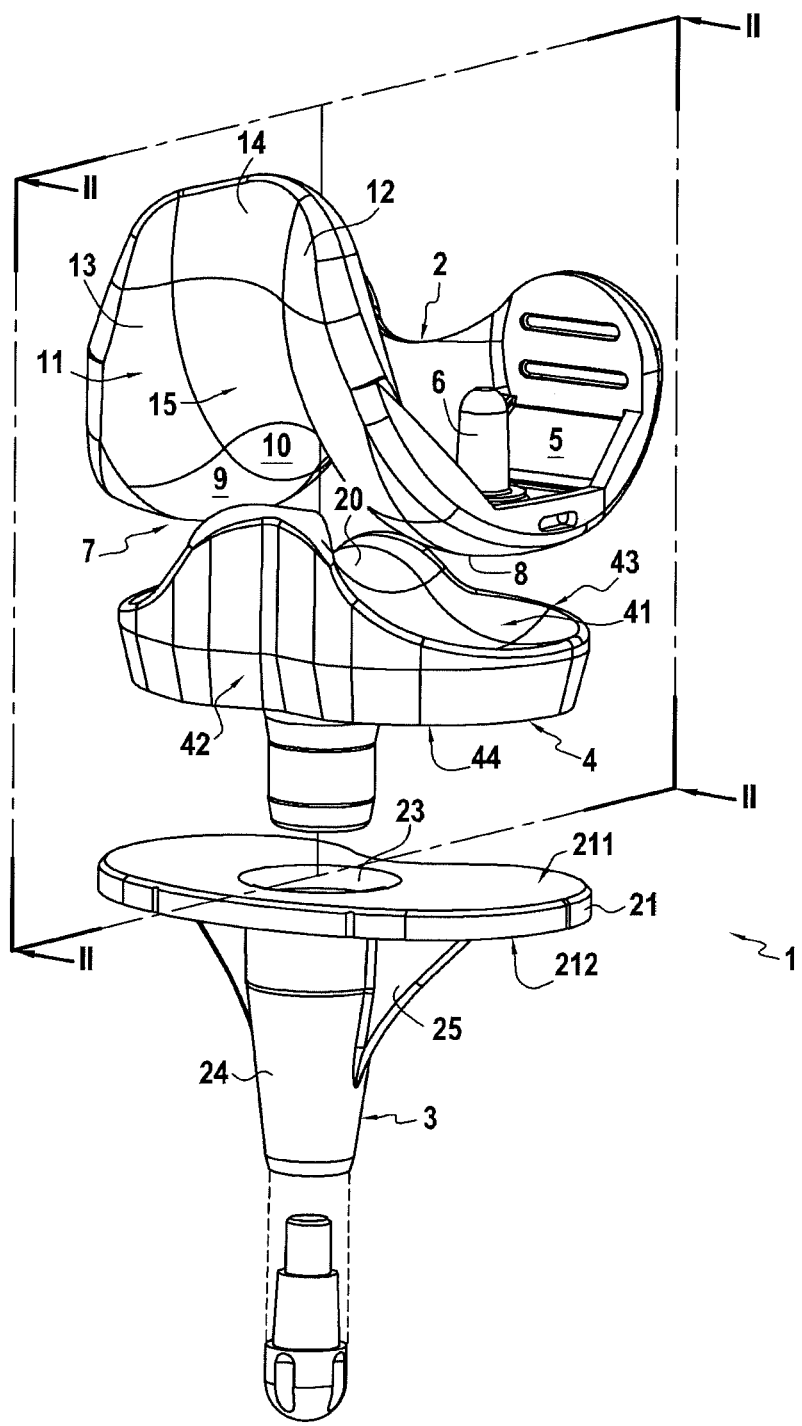
FIG. 1 shows in a perspective and exploded view, a total knee prosthesis according to the present invention, in a preferred embodiment.

As this is visible in FIG. 1, the insert 4 through its lower face 44 is supported on the upper surface 211 of a plate 21 of the tibial implant 3 and is rotationally mobile on this plate 21 about an axis which, in the position of use of the prosthesis, is positioned vertically and is materialized by a pin 22 extending and protruding from the lower surface 44 of the insert 4. This pin 22 is inserted into a central orifice 23 pierced in the plate 21 of the tibial implant 3, in a way known per se.

Figure 3:
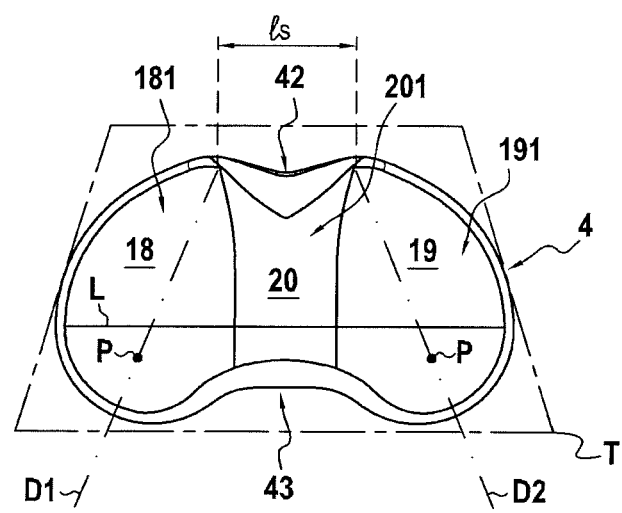
FIG. 3 is a top view of the articular insert of the prosthesis illustrated in FIG. 1
Figure 4:
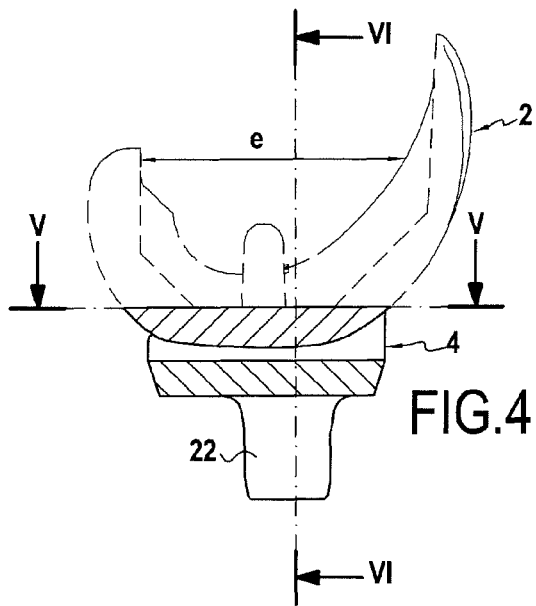
FIG. 4 is a longitudinal sectional view along a median sagittal plane II-II of the femoral implant and of the articular insert of the prosthesis of the invention.
Figure 5:
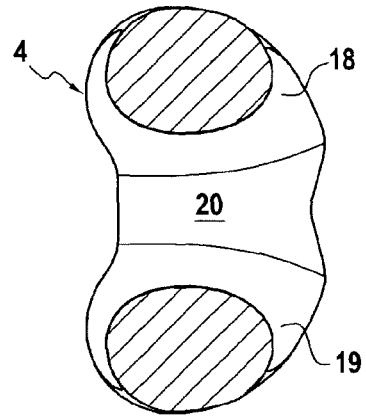
FIG. 5 is a sectional view in a horizontal plane V-V of FIG. 4, showing the ovoid contact surfaces between the femoral condyles and the glenoid cavities of the articular insert in the extension position of the prosthetic knee formed by the prosthesis of the invention, as well as the isthmian central contact area connecting both ovoid cavities.

Preferably the width Ii of the insert 4, taken in a horizontal section, is decreasing from its posterior face 43 towards its anterior face 42, said insert 4 thereby being inscribed in a trapezium T, as illustrated in FIG. 3. Thus the insert 4 does not jut out or only very little from the edges of the tibial plate 21 during these rotations on the latter, which prevents damaging of the preserved tissues for surrounding and stabilizing the prosthetic joint.

The tibial implant 3, as for it, also includes an anchoring medullar stem 24 extending from the lower face 212 of the plate 21 and intended to rest against a resected epiphyseal surface of the tibia (not shown). Preferably as illustrated in the figures, the orifice 23 for receiving the pin 22 of the insert is pierced and extends co-axially with the anchoring stem 24.

The tibial implant 3 also includes according to the invention, lateral reinforcements 25 firmly attached to the lower face 212 of the plate 21. Advantageously, these reinforcements are oriented towards the base of both gravitational wells P of the glenoid cavities 18, 19 of the insert 4. Such lateral reinforcements notably provide relief from the increases in stresses which tend to generate a torque loosening the tibial implant 3 during flexural movements of the prosthetic joint.

Conventionally, the femoral trochlea 11 of the femoral implant 2 is, as for it, capable of co-operating with the natural patella or with a patellar implant not shown.

Within the scope of the present invention, the proposed total knee prosthesis 1 also includes a patellar implant adapted for co-operating through an articular surface with the femoral implant 2. The articular surface of said patellar implant is in this case also defined along a hyperbolic paraboloid mating the one defined by the trochlear throat 14 and the intercondylar notch 10 of the femoral implant.

The patellar implant of the prosthesis of the present invention thereby allows continuous contact in the sagittal and horizontal planes with the femoral implant from the highest portion of the trochlea right up to the posterior portion of the condyles in all the flexural positions, the contact being made over the whole height and the whole width of the articular face of the patella.

The sliding of the patellar implant or of the natural patella, when it may be kept, is perfectly congruent with a contact over the whole surface of the implant and the trochlea and then the condyles, with continuous contact over the whole medio-lateral surface with the trochlea and the intercondylar area of the femoral implant.

The invention is not limited to the described and illustrated examples since various modifications may be made thereto without departing from the scope thereof.

The invention claimed is:

1. A total knee prosthesis (1) including:
a femoral implant (2) including two condyles (8, 9) delimiting between them an intercondylar notch (10), an external profile (101) of which is convex in a sagittal plane and concave in a frontal plane and is connected in all the planes without any discontinuity with an external profile (81, 91) of the condyles,
a tibial implant (3) including at least one supporting plate (21) intended to rest through a lower surface (212) thereof on the end of the tibia, if necessary after resection, and
an articular insert (4) interposed between the tibial implant and the femoral implant and capable of co-operating with them through lower (44) and upper (41) contact surfaces with shapes respectively mating an upper surface (211) of the supporting plate of the tibial implant and the external profiles (81, 91, 101) of the condyles and the intercondylar notch of the femoral implant,
the upper surface (41) of the articular insert including two glenoid cavities (18, 19) of the external profile (181, 191) congruent with the external profile (81, 91) of the condyles (8, 9) of the femoral implant and connected together through an interglenoidal connecting surface (20), with a shape congruent with the one of the intercondylar notch (10), and of an external profile (201) convex in a frontal plane and concave in a sagittal plane and connecting in all the planes without any discontinuity with the external profile (181, 191) of the glenoid cavities,
characterized in that the intercondylar notch (10) and the interglenoidal connecting surface (20) have congruent contact surfaces (101, 201), the contact surface (101) of the intercondylar notch (10) having a hyperbolic paraboloid shape and the contact surface (201) of the interglenoidal connecting surface (20) having a hyperbolic paraboloid shape mating the one defined by said intercondylar notch 10 and in that the contact surface (181, 191) of the glenoid cavities (18, 19) has in a horizontal section an ovoid shape and an inclined point (P) is located posteriorly to a line of larger width (L) of the insert, the concave external profile (201) in a sagittal plane of the connecting surface (20) defining a first high point at an anterior portion (42) and a second high point at a posterior portion (43), the first high point is higher than the second high point so that a straight line ($\Delta$) passing through the first high point and the second high point, has a slope from the anterior portion (42) towards the posterior portion (43) of the insert and in that this straight line forms an angle $\alpha$ comprised between 1° and 15°.

2. The prosthesis according to claim 1, characterized in that lowest points of the contact surface (181, 191) of the glenoid cavities (18, 19) of the insert are all located on a same straight line in a median plane of the insert.

3. The prosthesis according to claim 1, characterized in that ovoid contact surfaces (181, 191) of the glenoid cavities of the insert are connected, at each flexural level through an isthmian surface concave towards a front and rear in the hyperbolic paraboloid of the surface (201) of the interglenoidal connecting surface (20).

4. The prosthesis according to claim 1, characterized in that the width (Is) of the interglenoidal connecting surface (20), taken in a horizontal plane, is decreasing from an anterior portion (42) towards a posterior portion (43) of the insert.

5. The prosthesis according to claim 1, characterized in that a radius of curvature R2 of the external profile (201) for connecting the interglenoidal connecting surface (20) with the external profile (181, 191) of the glenoid cavities (18, 19) of the articular insert and the radius of curvature R1 of the external profile (101) for connecting the intercondylar notch (10) are substantially equal in common frontal planes so that the intercondylar notch (10) forms an imprint of the interglenoidal connecting surface (20) between both condyles (8, 9) of the femoral implant (2).

6. The prosthesis according to claim 1, characterized in that the width (Ii) of the insert, taken in a horizontal section, is decreasing from its posterior portion (43) towards its anterior portion (42), said insert being inscribed in a trapezium.

7. The prosthesis according to claim 1, characterized in that it includes a patellar implant adapted for co-operating through an articular surface with the femoral implant, the articular surface of said patellar implant being a hyperbolic paraboloid mating the one defined by the intercondylar notch.

8. The prosthesis according to claim 1, characterized in that the tibial implant (3) includes on its lower face of its plate (21), lateral stabilisation reinforcements oriented towards the base of the area supporting the condyles in the glenoid cavities of the insert when the knee is in a flexure position.

9. The prosthesis according to claim 1, wherein the angle is between 4° and 10.

* * * * *

UNITED STATES PATENT AND TRADEMARK OFFICE
CERTIFICATE OF CORRECTION

PATENT NO.         : 8,540,776 B2                          Page 1 of 1
APPLICATION NO. : 12/996161
DATED              : September 24, 2013
INVENTOR(S)        : Bercovy et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 209 days.

Signed and Sealed this

Fifteenth Day of September, 2015

Michelle K. Lee
*Director of the United States Patent and Trademark Office*